United States Patent [19]

Simons

[11] Patent Number: 5,224,674

[45] Date of Patent: Jul. 6, 1993

[54] METHOD AND APPARATUS FOR ORGANIZING AND IDENTIFYING INTRAVENOUS ADMINISTRATION LINES

[76] Inventor: Ramona K. Simons, 4620 S. Washington Rd., Saginaw, Mich. 48601

[21] Appl. No.: 845,113

[22] Filed: Mar. 3, 1992

Related U.S. Application Data

[63] Continuation-in-part of Ser. No. 678,015, Apr. 1, 1991, abandoned, which is a continuation of Ser. No. 452,838, Dec. 19, 1989, abandoned.

[51] Int. Cl.$^5$ .............................................. F16L 3/22
[52] U.S. Cl. ...................................... 248/68.1; 604/80
[58] Field of Search ............... 248/68.1, 67.5, 71, 248/73, 70, 72, 74.1, 62, 79; 211/60.1, 89; 604/80; 128/DIG. 26

[56] References Cited

U.S. PATENT DOCUMENTS

| | | | |
|---|---|---|---|
| 2,397,291 | 3/1946 | Robertson | 248/68.1 |
| 2,650,948 | 9/1953 | Findlay | 248/68.1 X |
| 4,308,642 | 1/1982 | Heyman | 248/68.1 X |
| 4,579,310 | 4/1986 | Wells et al. | 248/544 |
| 4,775,121 | 10/1988 | Carty | 248/68.1 |
| 4,795,441 | 1/1989 | Bhatt | 604/124 |
| 4,971,271 | 11/1990 | Sularz | 248/68.1 |
| 4,988,062 | 1/1991 | London | 248/68.1 |
| 5,043,746 | 8/1991 | Abe | 248/68.1 X |
| 5,085,384 | 2/1992 | Kasubke | 248/68.1 X |

FOREIGN PATENT DOCUMENTS 2620009 12/1977 Fed. Rep. of Germany .

Primary Examiner—Ramon O. Ramirez
Attorney, Agent, or Firm—Harness, Dickey & Pierce

[57] ABSTRACT

A device having a plurality of individual passages therethrough is removably attachable to appropriate supporting structure of a sickbed, adjacent equipments, or walls of the room. Each passage is adapted to non-deformably accept and retain a flexible tubing length of an individual intravenous medication administration line running from an associated medication supply reservoir to a patient. In one embodiment, each line may be independently placed into the device or independently removed therefrom through opening a covering surface to expose said passages. This cover may be a separate piece attached by way of hinges or may be a flap closable by way of a living hinge. The cover is provided with spaces onto which the content or nature of an associated intravenous administration line may be identified by erasably writing thereon. In another embodiment, a surface suitable for erasably marking is provided between the passages, obviating the need for a cover.

17 Claims, 5 Drawing Sheets

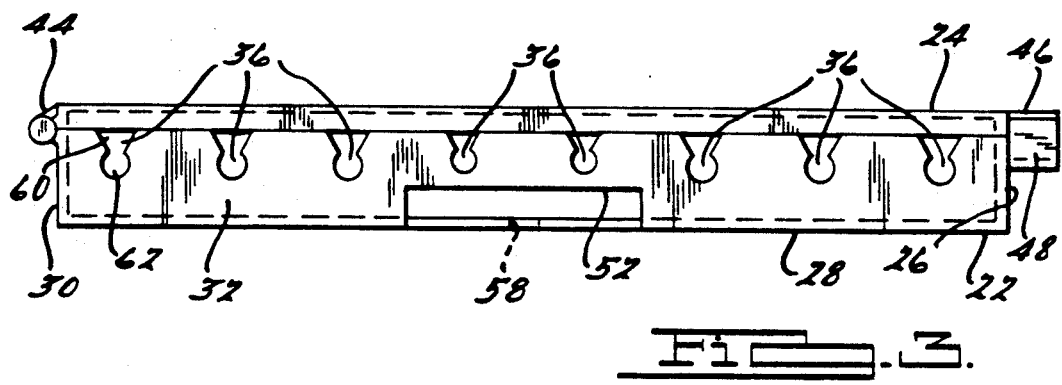
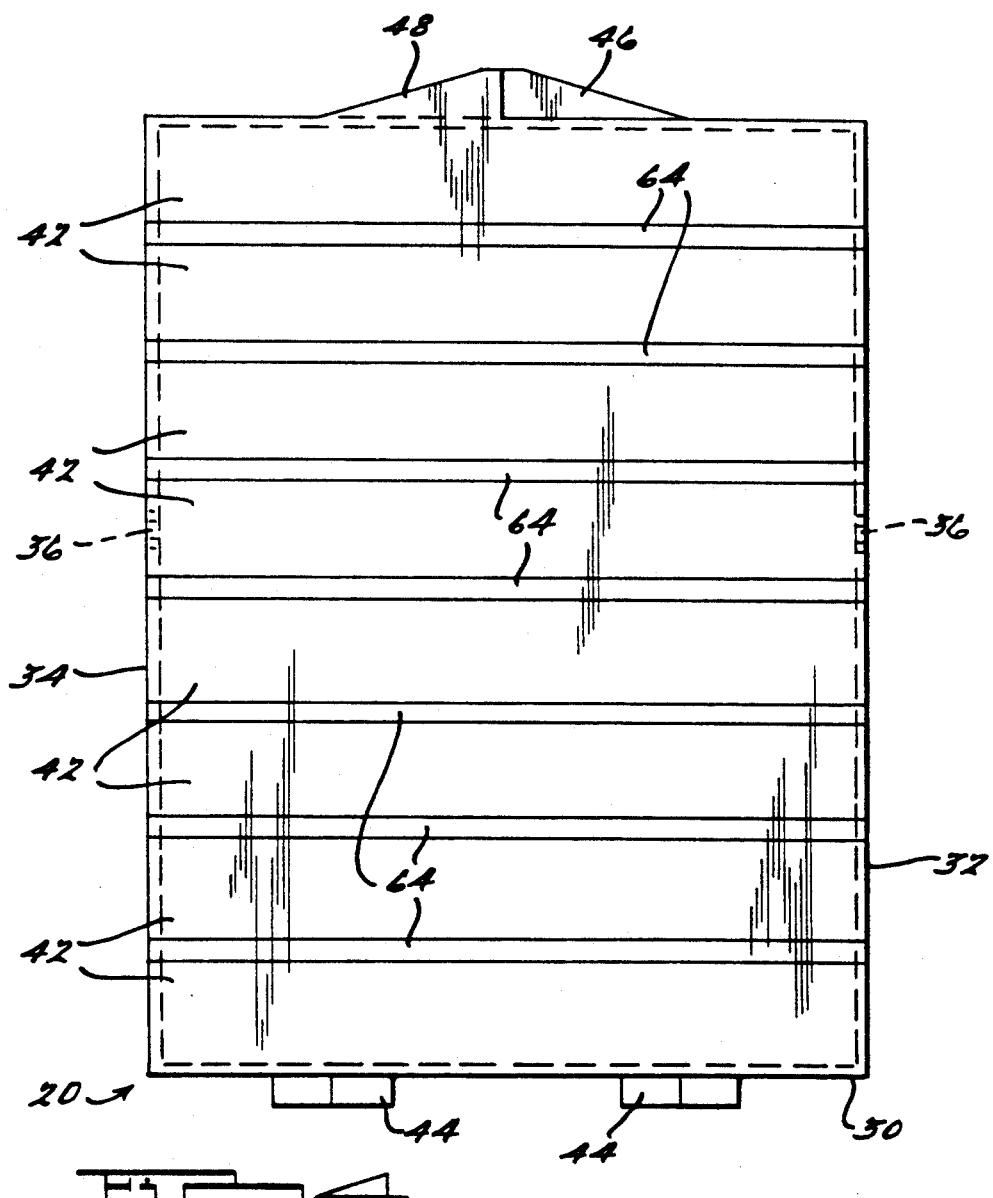

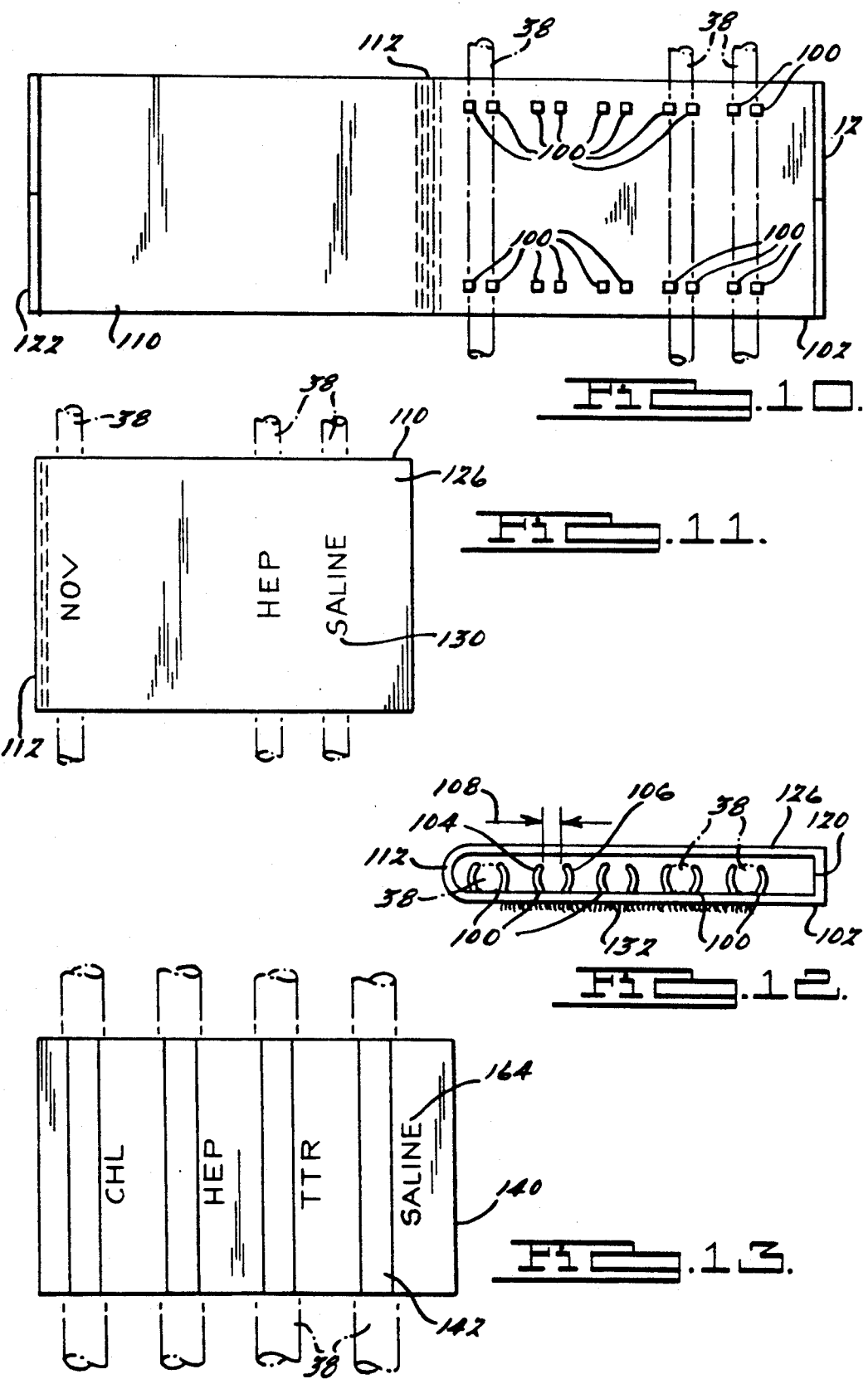

METHOD AND APPARATUS FOR ORGANIZING AND IDENTIFYING INTRAVENOUS ADMINISTRATION LINES

This application is a continuation-in-part of U.S. application Ser. No. 07/678,015, filed Apr. 1, 1991 now abandoned by Simons, entitled "Method and Apparatus for Organizing and Identifying Intravenous Administration Lines in Sickrooms" which was a continuation of U.S. application, Ser. No. 07/452,838, filed Dec. 19, 1989, now abandoned, and which was a revision thereof submitted individually by the second named inventor identified in said first in time prior application.

FIELD OF THE INVENTION

This invention relates in general to methods and apparatus useful in organizing and identifying multiple medications provided to a patient, and more particularly for separating and maintaining cognizance of the particular contents of each of a plurality of intravenous medication lines directed to a patient.

BACKGROUND OF THE INVENTION

It is routine medical practice in most health care facilitates to treat and medicate a patient by introducing therapeutic agents, drugs, medicines, nutrients, and various other liquids directly into the blood stream of the patient through systems commonly known as intravenous (IV) administration systems. Indeed, it is not uncommon for a critically ill patient to have several such systems concurrently operative to provide differing treatment agents. In some acute cases, ten to fifteen, or even more, different intravenous administration systems may be simultaneously connected to the patient.

A typical, commonly utilized, intravenous administration system consists of a length of transparent tubing having a hollow needle coupled to each end. The needle on one end of the tubing is adapted to be inserted, through a sealing member, into a supply reservoir containing a prescribed medication or other prescribed liquid. The reservoir may be in the form of a bag or a bottle, and is generally suspended, with the coupling to the tubing at a lowest elevation, from a pole so as to be above the level of the patient, thus enabling gravity flow of the liquid into the tubing. The needle on the other end of the tubing is adapted to be insertable into a venous blood vessel of the patient, or into a device known as an infusion port coupled to a needle inserted appropriately into the patient. The length of the tubing associated with the intravenous administration system is typically significantly longer than that necessary to reach from the supply reservoir to the patient so as to allow for slack and accommodate remote placement of the supply reservoir relative to the patient and to accommodate patient movement and access to the patient by health care professionals.

Most such intravenous systems are used to communicate medications and the like at controlled dosage rates. The most basic manner of controlling the dosage rate through a particular intravenous administration system is to place an adjustable clamp on the tubing at an appropriate location along its length, the clamp serving to partially or completely transversely compress the tubing so as to decrease the flow therethrough. More sophisticated intravenous administration systems include a monitoring mechanism which can responsively monitor and adjust the flow rate through the tubing, a portion of which is passed through the mechanism. Some such mechanism may even provide for an intermittent periodic introduction of a controlled dose of a particular prescribed medication.

As indicated hereinabove, an acutely ill patient may be subjected to concurrent medication through a plurality of intravenous administration systems, some directed to individual intravenous needles and others combined to flow through a common shared needle by inserting one of the systems into a branched infusion port. Sometimes a single needle inserted into the patient will be utilized to communicate a multiplicity of different medications, each entering the needle terminus portion through a separate, sequentially deployed, infusion port.

Common features of presently used intravenous administration systems include the need for maintaining sterility of the component elements up to the time of installation to the patient. Minimization of all risks of infection is paramount, since the typical patient usually has enough adverse conditions without adding any through mishandling or soilage of the intravenous administration systems. Thus, the tubing portions are normally available in acute sickrooms in the form of pre-packaged, sterile lengths, with attached sterile needles. Additionally, use of an intravenous administration system, particularly when multiple systems are being used, quite often arises in very serious or life threatening situations, wherein every second of time can be crucial. Time cannot usually be spared to enable trimming component lengths for neatness. The entire tubing length is utilized, even if such excess length results in adding a significant length portion to a tangle of tubing from other intravenous administration systems. Clearly, it does not require the addition of a very large number of intravenous administration systems before the health care professional performing the installation procedures will lose direct cognizance of the specific contents of each intravenous administration system unless reference is made to the identifications on the several supply reservoirs.

Since care of such acutely ill patients is substantially a continuously on-going task, several different health care professionals will be given primary care responsibilities for a given patient during each twenty-four hour time period. Moreover, each health care professional is likely to have primary care responsibility for more than one such patient. Further complication arises when it is recognized that relief health care professionals will, from time to time, become involved with a given patient during meal and rest periods of the primary care professional, and the recognition that the onset of critical episodes requiring heroic measures will bring a number of additional health care professionals into the treatment pattern, the additional personnel lacking the detailed cognizance of the intravenous administration systems, their specific contents, and their mutual relative organization. In each instance, in order to accomplish immediate medical orders, it is often necessary to locate the intravenous administration system providing a particular medication to the patient so that system may be unregulated, discontinued, or overdriven by a forced flow from contraction of the supply reservoir.

Heretofore, critical moments have been expended to trace the intravenous administration systems from their respective supply reservoirs to at least the location along the length of the tubing at which the clamp is deployed in order to perform the ordered emergency control of the proper intravenous administration system. Some health care professionals have recognized the potential time consumption of such tracing operations, and have devised individual solutions, such as taping each line to a bed rail or other structure, and by writing the name of the contents of a particular system on the corresponding tape holding its tubing in place. Another expedient used where allowed is to place a similar tape identification tag around the tubing near the patient. However, none of such individually improvised measures have achieved a level of acceptance that would indicate development of a standard procedure or approach that could be adopted for use by all health care professionals and institutions.

It has become apparent from the above that a device for organizing and identifying a plurality of intravenous administration lines, which device can be readily relocatably deployed in a sickroom setting, and which can be discarded upon completion of its use, would be advantageous. The inventor herein is not aware of any such device that is fully suitable for adaption to perform the desired medical functions, and suited to meet the objectives of the present invention. Those devices of a similar nature that may be found in the prior art presently within the knowledge of the applicant reside principally within those classes of technology addressing support clamps for electrical wires or cable, with a lesser number of references considering support brackets for plumbing systems. Examples of such prior art can be identified in the following briefly described references, which are not exhaustive of the totality of similar references.

An early, complex, holder for a plurality of wires is provided by the "Wire Holder" of the patent to Findlay, U.S. Pat. No. 2,650,948, issued Sep. 1, 1953. Upwardly extending arms disposed on either side of an elongated base element are provided with a plurality of notches accepting individual wires therein, the notches of one arm being in transverse registration with corresponding notches of the other arm. The base element may be rigidly attached to a supporting structure, typically using screws. A cover bar, configured to fit between the pair of arms, is hinged to one end of the base element so as to pivot downwardly between the arms and against wires held in the notches. The opposed end of the base element is provided with a pivoting clasp member adapted to engage a spring element on the cover bar. Each of the wires thus held are slightly deformed between the upwardly extending arms so as to rest on the base element, thereby rigidly affixing such wires in position, including precluding motions of the wires in their respective longitudinal directions.

Wilmes, in U.S. Pat. No. 4,253,629, issued Mar. 3, 1981, describes a "Guide and Marking Member for Electrical Cables". In this device, resiliently deformable wings, having a mutually dihedral relationship with adjacent wings, are supported from a base portion such that an electrical cable may be forced between pairs of wings and against the base portion so as to be captured and held in an aperture area extending transversely of the base portion. A separable plate element, containing an identification of a particular cable, may be snapped into a preformed recess on the obverse surface of the base portion. It appears from the teaching of Wilmes that this device is often to be utilized in a freely suspended manner intermediate of the length of the cable passed therethrough.

U.S. Pat. No. 4,579,310, issued Apr. 1, 1986 to Wells, et al., for "Guides for Organizing Wires", teaches the construction of an integral plastic strip formed into a comb-like piece having an elongated row of upstanding teeth or tabs, with an arcuate cove-like aperture formed at the roots between adjacent teeth. An electrical wire or cable may be forced into a cover to be captured and held securely therein, with the elongated plastic strip being appropriately attached to a supporting structure, thereby providing a supporting guide for a plurality of such electrical wires or cables. Deployment of similar plastic strips in a spaced apart manner along the course of such plurality of wires enables the wires to be extended along their path in a neatly organized manner. Similar plastic strips may be stacked at each location to provide organization for multiples of the plurality held by a single plastic strip. The tabs between coves provide locations where the nature of the adjacent wire or cable may be identified, although space for such identification is limited.

A "Cable Support with Tines" has been patented by Muz as U.S. Pat. No. 4,660,790, issued Apr. 28, 1987. This device, intended for providing separation between elements of a plurality of cables, consists of two mating elements of substantially identical configuration. Each element comprises an elongated strip with a plurality of upstanding tines spaced apart along an upper surface. A notch is formed on one end of a lower surface, obverse to the surface bearing the tines. The tine at the opposed end is formed to extend upwardly for a distance equivalent to the thickness of the base portion and to then extend parallel with the top ends of the tines for a distance matching the extent of the notch formed at the other end of the element. Taking a pair of such elements, inverting one of the elements to have its tines directed in a downward direction, placing a plurality of cables individually into the spaces between tines, the upper element is then translated along the length of the cables so as to engage its lip with the notch of the other element while its notch is being engaged by the overlapping lip of the other element. When the elements are so engaged, the several cables pass through substantially rectangular areas between the matched tines. It would appear that this device is primarily useful as a freely suspended organizing device, without intent to attach it to supporting structure.

U.S. Pat. No. 4,775,121, issued Oct. 4, 1988 to Carty, for "Cable Clamp", describes a clamp having a plurality of cable supporting arcuate notches, the device being substantially integrally formed with a covering bar to enclose the arcuate notches. The cover bar is coupled, at one end thereof, to the notched portion by a flexible hinge portion capable of allowing the other end of the cover bar to be laterally translated with respect to the notched portion. The free end of the cover bar is provided with a barb-like protrusion which engages a similarly formed female opening formed laterally in the notched portion. A visible recessed area is provided on the exterior surface of the cover portion into which an elongated strip may be placed to identify the contents of cables passing through the individual arcuate notches, the strip being held in the recess by a transparent cover held in the recess by friction.

Kraus has devised a "Plastic Holding Element" for fastening at least one pipe or tubular member to a supporting structure, which device is described in U.S. Pat. No. 4,881,705, issued Nov. 21, 1989. This device comprises a base portion and a cover portion, the cover being integrally formed with the base portion and attached thereto by a flexible hinge portion. The base portion is further formed to include a plurality of transversely oriented semi-circular channels, not necessarily of equal radius, accepting pipes to be supported. The cover portion is further formed to have a partially deformable pad element thereon which securely holds the pipes in their channels when the cover is closed. The free end of the cover portion is provided with a clasp engaging a mating clip on the base portion, While the surface of the cover portion appears to have a significant surface area, Kraus does not appear to consider using this surface to identify the pipes.

As indicated earlier herein, other references appear in the prior art. In each of these devices, including those described hereinabove, organization of a plurality of conduits appears to rely upon securely grasping the individual conduits, most often through a mechanism that applies transverse pressure on the individual conduits, which, in the case of a flexible fluid conducting conduit, may adversely affect the flow rate through such conduits. It also appears that, apart from manufacturing complexities, each of the prior art devices are intended to be used for extended periods, and reused as required. Identification of individual conduits passing through such devices is, where considered, of a permanent nature, and most of such devices provide only limited areas for inscribing such identifications.

Accordingly, it would be advantageous is to provide a method for organizing and identifying a plurality of independent intravenous administration systems.

It would be further advantageous to provide a method for organizing a plurality of independent intravenous administration lines, said method utilizing a pre-formed and preassembled organizing device that is readily attachable to a convenient supporting surface proximate to a patient in a sickroom setting.

It would be desirable to provide a method for identifying a plurality of independent intravenous administration lines, utilizing a pre-formed and preassembled organizing device that provides a surface for erasably indicating the content and/or destination of each intravenous administration line passing through such an organizing device.

It would be desirable to provide a pre-formed and preassembled device capable of retaining elements of a plurality of independent intravenous administration lines in a discrete relative relationship.

It would be further desirable to provide a pre-formed and preassembled device capable of accepting written indicia of the contents of individual intravenous administration lines passing therethrough in a discretely organized relative mutual relationship.

It would be advantageous to provide a pre-formed and preassembled device retaining individual elements of a plurality of intravenous administration lines without appreciable deformation or constriction of either or any of said individual intravenous administration lines of said plurality.

It would be further advantageous to provide a pre-formed and preassembled device for organizing and identifying elements of a plurality of intravenous administration lines into a discrete relative mutual relationship, which device is readily, relocatably, attachable to a convenient supporting surface or structure proximate to a patient to whom such plurality is directed.

It would be further advantageous to provide a pre-formed and preassembled device for organizing and identifying individual elements of a plurality of intravenous administration systems which device may readily be sterilized and packaged for rapid deployment and attachment when use thereof is required.

It would be desirable to provide a pre-formed and preassembled device for organizing and identifying elements of a plurality of intravenous administration lines, which device may be readily fabricated at a minimal expense sufficient to enable discarding such a device upon completion of its use in association with treatment provided to an individual patient.

SUMMARY OF THE INVENTION

The present invention provides for an intravenous tube retention device having a readily accessible surface for identifying each intravenous tube. The surface is erasable to allow for corrections or changes in the identification information. The surface is also readily visible to provide hospital personnel with a convenient and expedient manner of identifying individual intravenous lines. The device can be attached to any convenient structure such as the patient bed or intravenous medication administration pole, allowing the intravenous administration system to be easily transported. Since the device can be mounted to any number of structures, the device also functions to secure the intravenous tubes without allowing the tubes to become entangled with each other or with other equipment. Also, the risk of an intravenous tube draping across the floor is reduced, helping to prevent accidental yanking of the tubes and reducing the likelihood of infection transmission that may otherwise result from the tube touching the floor.

These, and other objects, features, and advantages of the present invention and the associated methods will become evident through the subsequent descriptions and claims.

BRIEF DESCRIPTION OF THE DRAWINGS

In the accompanying drawing, wherein like reference numbers and symbols are used to refer to like components and features throughout:

FIG. 3 illustrates a side view of a device for organizing and identifying individual elements of a plurality of intravenous administration systems in accordance with the present invention;

FIG. 4 provides a top view of the cover portion of the device of FIG. 1;

FIG. 10 is a top view of an alternative embodiment of the device, showing the cover portion in the open position;

FIGS. 11 and 12 are top and side views, respectively, of the device of FIG. 10 with the cover closed;

FIGS. 13 and 14 are top and side views, respectively, of another alternative embodiment of device employing surfaces between the intravenous tubes for identifying the tubes.

DESCRIPTION OF THE INVENTION

General Description of the Invention

Figure 1:
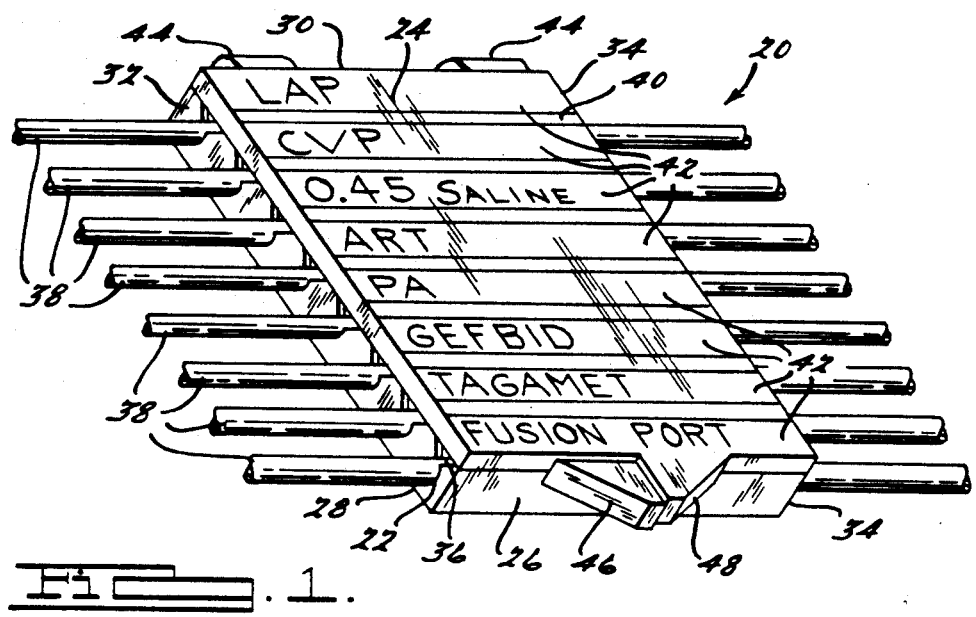
FIG. 1 presents a perspective view of a device for organizing and identifying individual elements of a plurality of intravenous administration systems in accordance with the present invention.

In one embodiment of the invention, a device for retaining and identifying intravenous administration lines comprises a lower bed portion having a longitudinal extent bounded by raised end portions, each side of the longitudinal extent being formed to have raised side members, and a cover portion integrally formed with said bed portion and coupled thereto at one end by a flexible hinge portion. The free ends of the bed portion and the cover portion are provided with mating frictionally engaging portions to hold the cover portion to the bed portion in a closed direction. The raised side members of the bed portion are mutually spaced apart by a convenient width dimension of the bed portion, typically between two and three inches, said width being suitably adapted to enable attachment of the bed portion to a supporting structure. The raised side members are formed to include a plurality of notches therein directed from the cover closing edges thereof toward a base member spanning the width between the raised side members. The notches of one side member being substantially uniformly spaced apart along the longitudinal extent of said side member, with corresponding notches formed in the opposed side member being constrained to be in like number and in correspondingly transverse registration therewith. Each notch narrowing as it progresses toward said base member to terminate in an arcuate shape adapted to non-deformably accept the cross-section of a typical intravenous administration system flexible, transparent tube therein. Narrowing of the notch is limited to provide at least a minimum separation between edges of the notch that is only marginally less than the diameter of such flexible tubing. The cover portion is further adapted to have a number, equal to the number of notches in each side member, of delineated outer surface areas, extending transversely of the device, adapted to accept ball-point writing or grease pencil inscription, which writing may be removed by moist scrubbing action on the surface areas. Each such area is appropriately aligned with a corresponding opposed pair of notches, and is useful in inscribing the content of the tubing passing through said pair of notches. A lower surface of the bed portion is provided with means for attaching the device to a convenient supporting surface, which may be a bed rail, a portion of the bed structure, an adjacent area of a proximate sickroom wall surface, or a support standard for supply reservoirs of the applied medications. The attachment means may consist of, alternatively, a double adhesive faced pad; a hook and mating loop engagable pair of pads, each having an adhesive surface for attaching one mating half to the device and the other mating half to the supporting surface; or a strap linked to the base portion for tying around a supporting pole or other structural member.

The present invention also provides a method for organizing and identifying individual elements of a plurality of intravenous administration systems directed to a particular patient. When it is known that a patient is to receive a number of different intravenously administered prescribed medications or other liquid solutions, each at its appropriate continuous or periodically controlled dosage rate, a device as described hereinabove is secured, attached to an appropriately selected support surface or structure at a convenient location relative to the patient, to apparatus within the sickroom, and disposed with its cover unlatched and open. A first of the plurality of intravenous administration systems is traced from its supply reservoir to the patient, and an appropriate portion of the length of flexible tubing connecting the supply reservoir to the patient is engaged within a first opposed pair of notches in the side members of the device, allowing appropriate slack tubing length to accommodate patient positioning, movement, and access by health care professionals. The cover of the device is then closed and the identification of the content of that intravenous administration system is inscribed in the corresponding space on the cover portion of the device. Subsequently, additional intravenous administration lines are traced, one at a time, and inserted into another opposed pair of notches of the device, first opening the cover for insertion, and then reclosing the cover to inscribe the appropriate identification in the corresponding area on the cover. If more intravenous administration systems are being employed than the number of opposed pairs of notches of the device, a second, and further device is deployed, attached, and utilized as described hereinabove.

In the event that medical orders require a change in dosage rate of a particular medication, location of the proper intravenous administration line is facilitated by referring to the identifications written on the covers of the deployed devices, with tracing to the flow control mechanism being simplified by requiring tracing of only a portion of the length of the flexible tubing. Similarly, if a particular medication is to be discontinued, its supply reservoir is closed off, the tube therefrom is traced from the organizing and identifying device to its point of entry to the patient, the system is removed from the patient, the cover of the device is opened and the corresponding tubing portion is removed from its opposed pair of notches, the cover reclosed, and the identifying writing obliterated by moist scrubbing action. The discontinued intravenous administration system is then discarded. The notches of the device thus vacated are available for use by a newly prescribed system.

Addition of a new intravenous administration system to deliver a newly prescribed medication to the patient is accomplished in a manner similar to the initial set-up procedure. The supply reservoir of the new medication is coupled to a new flexible tubing assembly, with the other end of the flexible tubing inserted into the patient or an appropriate infusion port of another intravenous administration system. When proper dosage flow rate has been established, a portion of the flexible tubing is placed into a vacant opposed pair of notches in one of the devices, if available, and the cover thereof is closed. Identification of the new medication is then written on the cover in the corresponding surface area, and the supply reservoir appropriately suspended to maintain flow by gravity. If no vacant opposed pair of notches is available in any of the deployed devices, a further device is deployed and attached to the supporting structure.

Transfer of the patient to another location, or repositioning of the patient, or increased access to the patient in critical emergency situations can be accomplished without confusing the organization and identification of the several intravenous administration systems being used to treat the patient by merely relocatably detaching the device or devices then in use and placing them at more convenient locations or allowing them to hang freely until replacement at the original position is appropriate. Complete tracing of the several intravenous administration systems is thereby avoided.

At such times as all intravenous administration systems are to be removed from the patient, separate disassembly of each system is not required. The health care professional need only remove all intravenous needles from the patient, all supply reservoirs from their supports, and all organizing and identifying devices from their supporting surfaces, and thereafter discard the entire combination of systems, following any appropriate safety regulations.

Further embodiments of an organizing and identifying device for a plurality of intravenous administration systems may appear from the preceding. Each such further embodiment must provide satisfaction of the essential characteristics of grouping transmission lines of the several administration systems such that the tubing associated with a particular system is in a particular location at which identification of the nature of the contents of that system are identified. All such reasonable, equivalent alternate embodiments are to be construed as being within the scope of the present invention.

Detailed Description of the Preferred Embodiments

Referring first to FIG. 1, a device for organizing and identifying individual lines of a plurality of intravenous administration systems is indicated generally at 20. The device 20 can be noted to comprise a lower-bed portion 22 and a cover portion 24. The bed portion 22 is integrally formed to have a first end 26, extending upwardly from a bottom planar element 28, a second end 30, opposite said first end 26, and upwardly extending side elements 32, 34, each side element 32, 34 formed to include a plurality of retaining elements formed as notches 36 adapted to accept individual flexible tubing lines 38, each associated with a respective independent intravenous administration system (not illustrated). The notches 36 formed in the side element 32 are substantially equidistantly spaced apart with respect to the extent of the device 20 between the first end 26 and the second end 30. The notches 36 formed in the opposed side element 34 being in like number and in transverse registration with the notches 36 formed in the side element 32 so as to provide a corresponding plurality of paths across the device 20, each path being substantially parallel to the first end 26 and the second end 30. Each path thus defined being associatedly available to accept one of the aforesaid flexible tubing lines 38.

The cover portion 24 is adapted to fully span an area bounded by upper lips of the first end 26, the second end 30, and the opposed sides 32, 34, and is formed as a substantially planar element having an upper outer surface 40 segregated into a plurality of substantially rectangular surface areas 42. Each such rectangular area 42 is formed in a manner that is adapted to accept written information, as illustrated in FIG. 1. Each rectangular area 42 is associated with a corresponding path assumable by a flexible tubing line 39 so as to provide a positive written identification of the nature of the line 38 passing through the associated path between the corresponding notches 36 of the opposed sides 32, 34.

Figure 2:
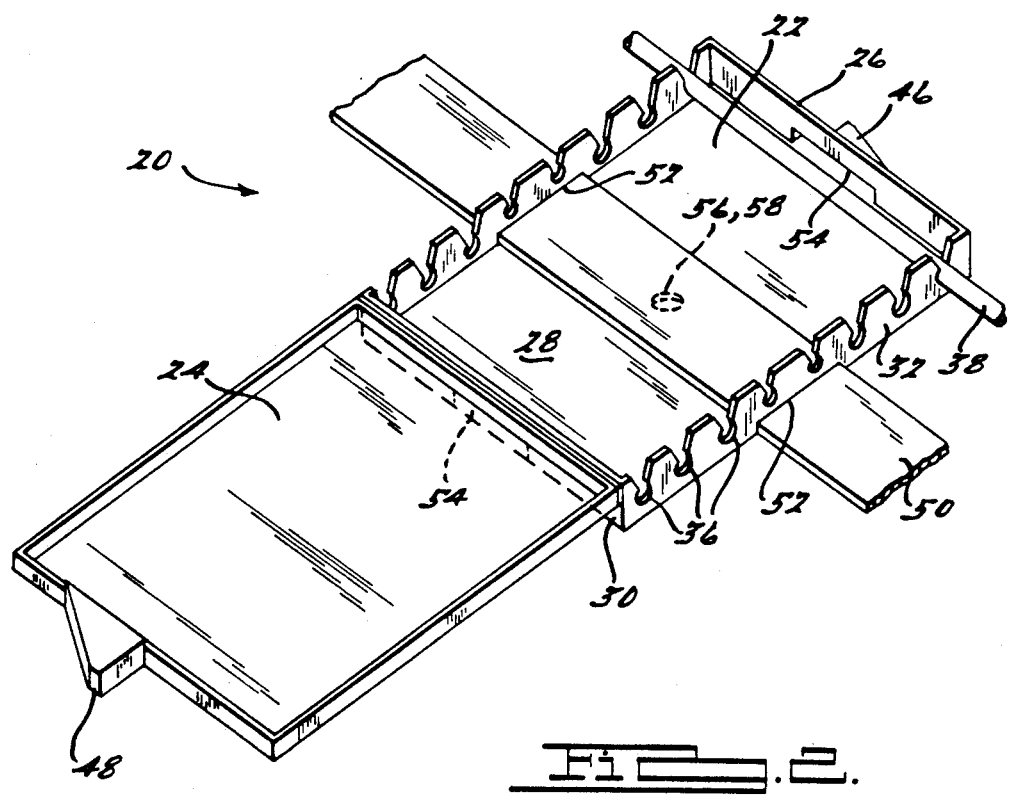
FIG. 2 presents a perspective view of the device of FIG. 1, showing a cover portion in an opened position.

Hinges 44 are typically formed on the second end 30 of the bed portion 22 to mate with corresponding mating structure formed on the corresponding end of the cover portion 24. The hinge structure 44 may be integrally formed with both the bed portion 22 and the cover portion 24 so as to provide a single element construction for the device 20. The first end 26 of the bed portion 22 is integrally formed to include an upwardly projecting structure 46 which is adapted to cooperatively engage with a downwardly extending structure 48 integrally formed on the corresponding end of the cover portion 24 so as to form a frictional clasp to releasably hold the cover portion 24 to the bed portion 22. Referring next to FIG. 2, the device 20 is shown with the cover portion 24 open relative to the bed portion 22, and with only one of the plurality of lines 38 of FIG. 1 being shown. From this perspective illustration of the device 20, the transverse registration of the notches 36 formed in both the opposed side elements 32, 34 can be clearly observed. Additionally, a first embodiment of a manner of attaching the device 20 to a supporting structure (not shown) is provided by a strap 50 passed through slots 52 formed in the opposed sides 32, 34, said slots 52 being proximately above an inner surface of the bottom planar element 28. An alternate pair of slots 54 are formed, in substantial longitudinal registration, though the first end 26 and the second end 30 of the bed portion 22. The strap 50 is readily relocatable from passage through the side slots 52 to passage through the end slots 54 so as to accommodate attachment of the device 20 to various supporting structure (not shown). The strap 50 is provided with an extent appropriate to pass around such supporting structure, with each longitudinal end of said strap 50 being appropriately terminated with mating fastening elements to hold said ends of the strap 50 together. Typically, such means for holding the free ends of the strap 50 together may be in the form of a buckle, or in the form of mating hook and loop type fasteners, or any similar standard fastening method, without affecting the nature of the device 20. A further alternate embodiment of attaching the device 20 to appropriate supporting structure is indicated by the alternate inclusion of a snap element 56 on the strap 50, which may engage with a mating snap element affixed to the inner surface of the bottom planar element 28 of the bed portion 22, or, in a further alternative embodiment, with a mating snap element (not illustrated) affixed to the supporting structure, with a hole 58 being formed through the bottom planar element 28 in registration with the snap element 56 attached to the strap 50.

It is also of interest to note that the bed portion 22 shown in FIG. 2 may be formed without a bottom planar element 28 so long as the slots 52 through the sides 32, 34 and the slots 54 through the ends 26, 30 are formed to be substantially rectangular openings not intersecting lowermost edges of the sides 32, 34, or ends 26, 30.

Referring next to FIG. 3, an end plan view of the device 20 is given, as viewed from the left of FIG. 1 or from the lower right aspect of FIG. 2. In this illustration, the cover portion 24 is shown as closed upon the bed portion 22 with the hinges 44 to the left and the clasp structures 46, 48 to the right. Each of the notches 36 formed in the side element 32 are shown to be shaped as a generally V-shaped opening 60 decreasing from an upper lip of the side element 32 to an arcuate opening 62 having a substantially circular area. The dimensions of the arcuate openings 62 are adapted to be substantially identical with an outer diameter of a flexible tubing intravenous line (not shown) to pass therethrough such that said flexible tubing is not constricted by resting within said arcuate opening 62 of its notch 36. The corresponding dimension of the narrowest region of the V-shaped opening 60 of the notch 36 is generally adapted to be marginally less than the outer diameter of the flexible tubing of the intravenous administration system such that said tubing can be readily inserted into its corresponding arcuate opening 62 by pressing downwardly through the V-shaped opening 60, with the marginally reduced dimension serving to retain the tubing in its corresponding arcuate opening 62, without requiring any pressure from the cover portion 24 or associated structure.

Referring next to FIG. 4, the exterior surface of the cover portion 24, as viewed from the top of the device 20, is shown to be formed to have the aforesaid plurality of rectangular areas 42 adapted to accept appropriate identification markings for the line paths through the notches 36 therebelow. Each such rectangular area 42 is separated from adjacent rectangular areas 42 by separation areas 64 that are integrally formed, during fabrication of the cover portion 24, to be impervious to accepting writing thereon, thus clearly separating any identification writings entered into the appropriate areas 42.

Figure 5:
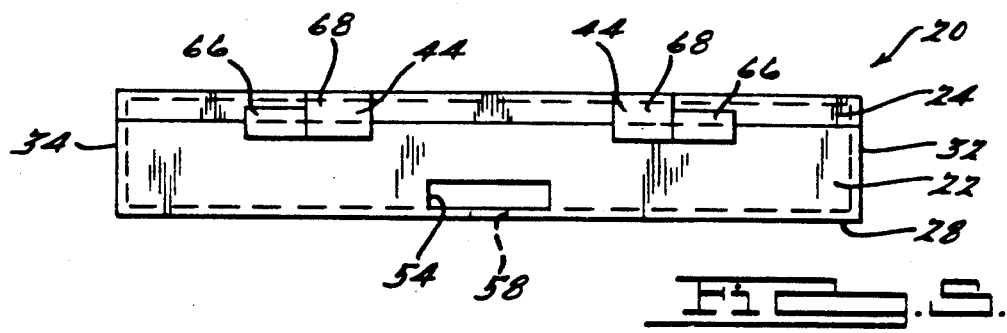
FIG. 5 is an end view of the device illustrated in FIG. 2.

Referring next to FIG. 5, illustrating an exterior end view of the device 20 from an upper left aspect of FIG. 1 or from a lower left aspect of FIG. 2, an alternate placement of hinges 44 may be noted. In such an embodiment, wherein the bed portion 22 and the cover portion 24 are formed as separate structures, the bed portion 22 is formed to include a pair of spaced apart upwardly extending half hinge structures 66, and the cover portion 24 is formed to include a pair of spaced apart downwardly extending mating half hinge structures 68, wherein the spacings of the structures 66 and 68 are such that the pairs engage with each other in a manner enabling the cover portion 24 to pivot upwardly about the upper lip edge of the second end 30 of the bed portion 22.

Figure 6:
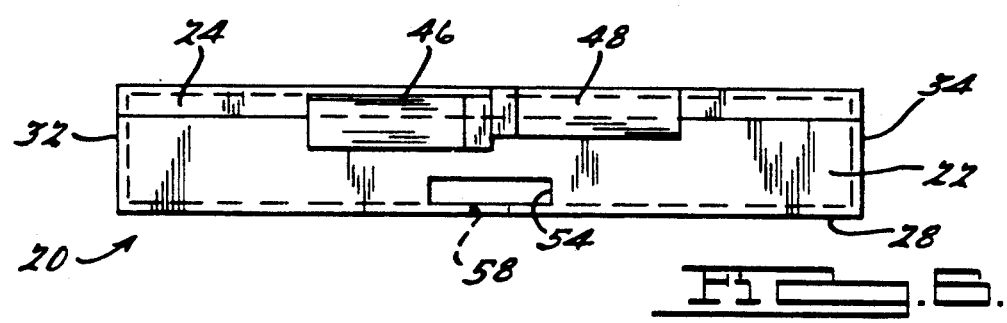
FIG. 6 is an end view of the opposite end of the device illustrated in FIG. 2.

Referring next to FIG. 6, an opposed end view of the device 20, illustrating the first end 26 of the bed portion 22 and the corresponding end of the cover portion 24, illustrates a first embodiment of a clasp mechanism for holding the cover portion 24 to the bed portion 22 when in a closed position. The clasp mechanism includes the aforesaid upwardly extending structure 46 formed integrally on the exterior of the first end 26 of the bed portion 22, and the frictionally mating downwardly extending structure 48 formed on the corresponding end of the cover portion 24. The primary frictional contact between the structures 46 and 48 is generally along adjacent surfaces of each structure shown as the separation line 70 illustrated in FIG. 6.

Figures 7, 8:
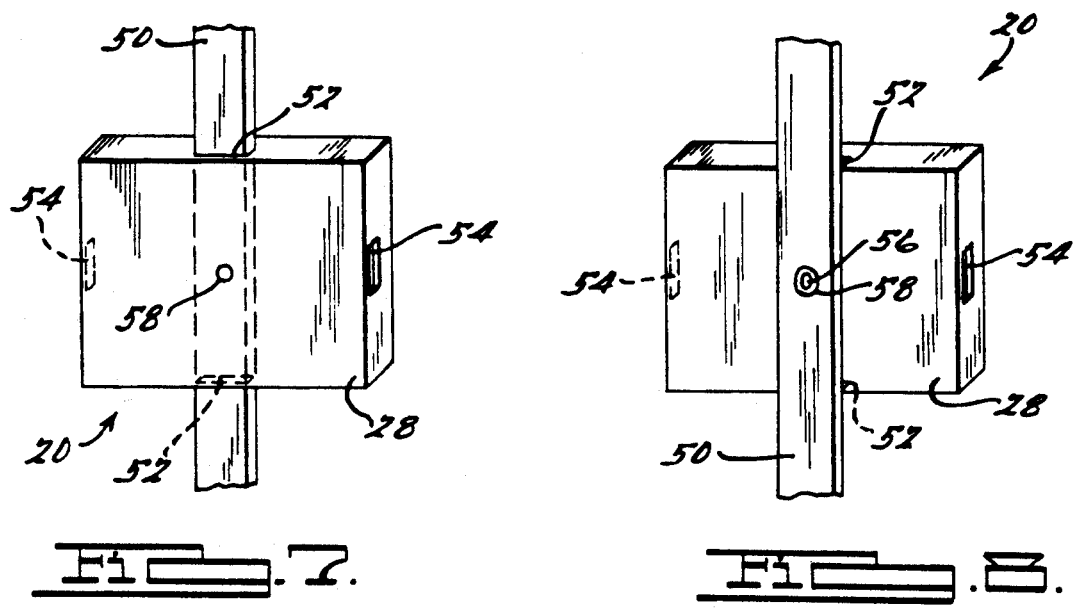
FIG. 7 presents a bottom perspective view of a device in accordance with the present invention, indicating a first embodiment of means for attaching said device to a supporting structure.
FIG. 8 presents a bottom perspective view of a device in accordance with the present invention, indicating a second embodiment of means for attaching said device to a supporting structure.

Referring next to FIG. 7, a bottom perspective view of the device 20 is presented to illustrate, more completely, a first method of deploying the device 20 to an appropriate supporting structure (not illustrated). The aforesaid strap 50 is shown to pass internally of the device 20 through the slots 52 formed in the opposed side elements 32, 34, said strap 50 being in close proximity to the inner surface of the bottom planar element 28 of said bed portion 22 throughout such passage through the device 20. Alternately, when the orientation of the supporting structure and the directions of progression of the intravenous lines so warrant, the strap 50 may be relocated to pass through the device 20 through the slots 54 formed in the opposed ends 26, 30 of the bed portion 22. In either case, the device 20 may be positionally coupled to the strap 50 by employing a snap connector 56, as previously described. In either case, the device 20 is held in position by passing the strap 50 around the supporting structure and linking together the free ends of the strap 50.

Referring next to FIG. 8, a second method of deploying the device 20 to an appropriate supporting structure (not illustrated) is presented. In this embodiment, a strap 50 is passed across either a width or a length of the device 20 externally adjacent the bottom planar element 28 of the bed portion 22. The positional relationship between the device 20 and the length of the strap 50 is maintained by a snap coupling 56 through the hole 58 disposed centrally through the bottom planar element 28 of the bed portion 22. It is to be noted that any desired angular relationship between the device 20 and the length of the strap 50 may be provided through this embodiment.

Figure 9:
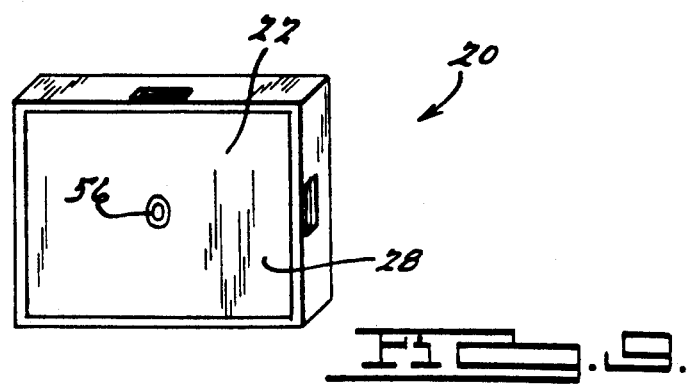
FIG. 9 presents a bottom perspective view of a device in accordance with the present invention, indicating a third embodiment of means for attaching said device to a supporting structure.

Referring next to FIG. 9, a third method of deploying the device 20 to an appropriate supporting structure (not illustrated) is presented. In this embodiment, the exterior surface of the bottom planar element 28 of the bed portion 22 is provided with a snap element 56 capable of matingly engaging with a mating snap element deployed adhesively on a surface of the supporting structure at the desired location thereon. Said illustrated embodiment may be further varied by providing the exterior surface of the bottom planar element 28 with an adhesive coating which may adhere directly with the supporting structure, or, in a further alternate embodiment, the exterior surface of the bottom planar element 28 may have an area of one element type of a mating hook and loop fastener adhesively attached thereon, with the other mating hook and loop element deployed and attached to the supporting structure at the desired position thereon.

In FIGS. 10-12, an alternative, preferred embodiment of the device is illustrated. Here, the flexible tubes 38 are retained by generally U-shaped retaining elements formed as retaining clips 100 spaced approximately equidistantly along opposing edges of a base member 102. As was the case in the previously described embodiment, the retaining clips 100 are located along the base 102 in opposing pairs so as to provide a path along which a tube 38 can be retained. The retaining clips include left and right tangs 104, 106 forming a U-shaped passage having an upper clip spacing 108 slightly smaller than the diameter of the tubing 38, thereby facilitating the retention of the tubing 38 within the retaining clip 100 without deforming the tubes. Although only five pairs of retaining clips 100 are illustrated here, it can be appreciated that any number of retaining clips could be employed depending upon the particular needs of the situation.

A cover "flap" piece 110 is integral to the base 102, with a living hinge 112 providing for the cover 110 to be flexed over the retaining clips 100 to enclose the tubing 38, as shown in FIGS. 11 and 12. As with the cover of the previously described embodiment, a frictional clasp 120 is provided, having frictionally interlocking opposing clasp tabs 122, 124. The upper surface 126 of the cover is suitable for marking 130 to identify the intravenous tubing 38, and the marking 130 can be erased using suitable erasing means such as a common abrasive eraser or by rubbing with a moistened towelette. It can be appreciated that a variety of marking and erasing means could be employed. Also, although this embodiment employs a hook-and-loop type fabric attachment system 132 for removably attaching the intravenous tube retaining device to suitable structures, it can be appreciated that a strap or snap as previously disclosed could also be employed.

Figure 14:
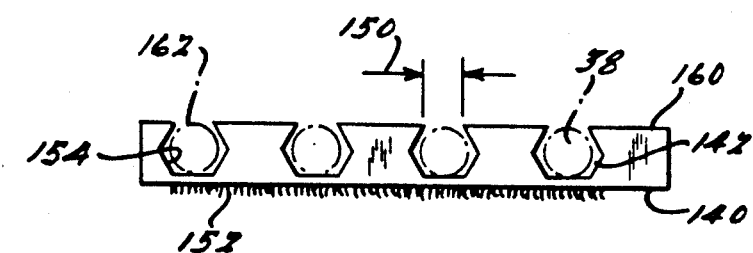

Yet another alternative embodiment is illustrated in FIGS. 13 and 14. Here, the base member 140 has a plurality of channels 142 formed along the face of the base 140, providing retaining element "slots" into which the intravenous tubings 38 are retained. Again, the retaining channels 140 have an upper opening 150 of a dimension slightly smaller than the diameter of the tubing 38 so as to retain the tubing 38 within the channel, while the somewhat hexagonal channel 154 itself is slightly larger than the diameter of the tubing 38 so as to avoid deforming the tube or constricting the flow of fluids within the tubing. The upper surface 160 of the base 140 lies flush or even slightly above the level of uppermost edge 162 of the retaining tubing 38 and provides a readily accessible surface for erasably marking 164 to identify the various intravenous tubes 38 retained within the device. While a hook-and-loop type fabric attachment system 152 is employed, it can be appreciated that any number of means could be employed for removably attaching the device to a suitable structure.

Figure 15:
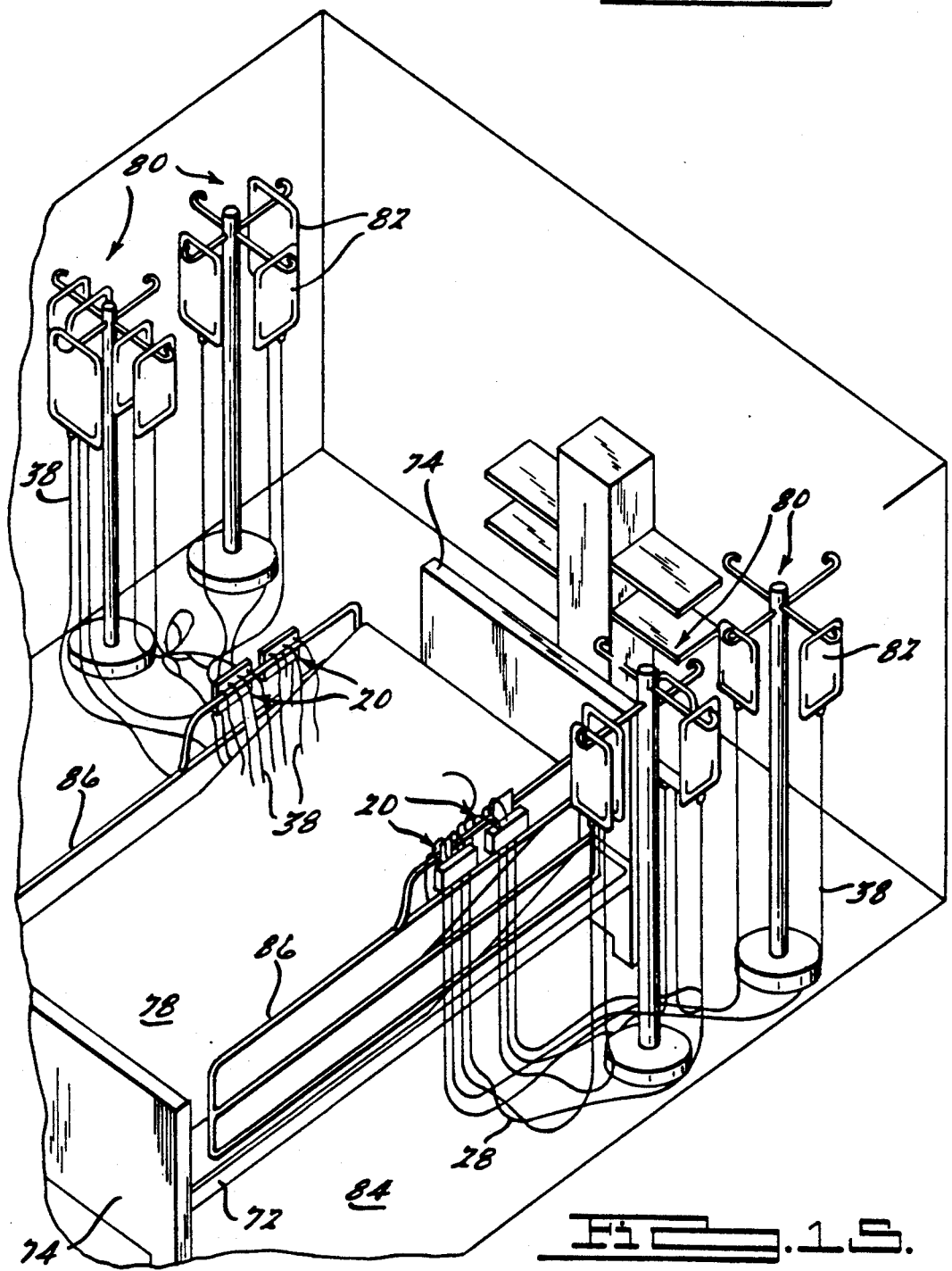
FIG. 15 illustrates, in perspective, an overview of a sickroom indicating a deployment of a plurality of intravenous administration systems utilizing devices in accordance with the present invention.

Referring lastly to FIG. 15, a perspective overview of a sickroom setting, wherein a multiplicity of devices 20 are deployed, is provided to illustrate a method of organizing and identifying individual intravenous administration system transmission lines 38 for a large plurality of such systems being used to provide medications and other treatment to a patient. As so illustrated, a patient is disposed in a bed 72, having a footboard 74 and a headboard 76 for reference, with his or her head generally disposed to be on a mattress 78 or other support proximate to the headboard 76. A plurality of support standards 80 are illustrated in several deployed position proximate to the bed 72, each standard 80 supporting several different supply reservoirs 82 for appropriately prescribed medications. Each supply reservoir 82 is illustrated to be coupled to a corresponding flexible tubing line 38 directed to the patient, with excess tubing being allowed to hang freely, in a disorganized manner, on the floor 84 of the sickroom. Intermediate of the extent of each flexible tubing line 38, the line 38 is passed through one of the paths through one of the devices 20 deployed conveniently from bedrails 86 of the bed 72. As each line 38 is passed through its corresponding path through its corresponding device 20, the content of that line 38 is noted on the corresponding area 42 of the cover portion 24 of the corresponding device 20, in the manner suggested by FIG. 1. From the device 20, the line 38 continues to the patient or to an appropriate infusion port 88 shown to the left of the patient position on the bed 72.

With reference to the several Figures of the drawing as may be appropriate, a method for organizing and identifying individual intravenous administration systems is provided by tracing a given transmission flexible tubing line 38 from its supply reservoir 82 to an extent allowing an appropriate residual length for administration to the patient, at which extent a device 20 in accordance with the present invention is appropriately deployed and attached to supporting structure of a sickbed 72 or equivalent structure, a length of the flexible tubing line 38 is pressed downwardly into the corresponding retaining element (60 or 100 or 142) until the line 38 is fully seated and retained within the retaining element, whereupon the contents of the so deployed flexible tubing line 38 can be written, in an erasable manner, on the corresponding area and the free end of the flexible tubing line 38 coupled to the patient. Subsequently, a second, and further additional, intravenous medication administration systems may be deployed to have their respective supply reservoirs 82 on the same or other support standards 80, with the respective flexible tubing lines 38 being individually traced to an extent appropriate for insertion into a next available retaining elements in the same or another device 20, whereas notation of the content of the particular line 38 is made in the corresponding area of the device 20 so utilized. When a particular medication is discontinued upon medical order, its flexible tubing line 38 may be identified from the identifying writing on one or another of the devices 20 being utilized for the patient, the identification is then erased or obliterated, the line 38 removed from the retaining element in the device 20, the system removed from the patient and, along with its supply reservoir, discarded in accordance with standard medical procedures. The retaining element thus vacated may be utilized to identifiably organize any newly prescribed medication to be applied to the patient intravenously. When all intravenous medications are terminated, after the patient has been disconnected, all lines 38 and supply reservoirs 82 may be discarded en masse by detaching the devices 20 from their respectively appropriate supporting structures, for disposal thereof without removal of the several lines 38 from the devices 20.

While the foregoing detailed descriptions provide several variant embodiments of the basic device 20 in accordance with present invention, it is recognized that additional modifications in the particular shapes and manner of attachment may become apparent. Each of such further alternate embodiments and reasonable equivalents thereof are considered as being within the scope of the present invention, which shall be limited only by the scope of the claims appended hereto.

I claim:

1. A device for retaining a plurality of flexible intravenous tubes capable of carrying fluids, to reduce tangling of the intravenous tubes and facilitate ready identification of each intravenous tube, the device comprising:

means for retaining the intravenous tubing, said retaining means adapted to retain the intravenous tubing without deforming or restricting the flow of fluids within the tubing and allow for ready removal of the tubing, said retaining means having a surface suitable for being directly writingly marked upon to identify each of the intravenous tubes, said surface also adapted for removal or alteration of said markings, said surface being readily accessible for both marking and reading said markings while the intravenous tubes are retained; and means for attaching the device to a structure.

2. The device of claim 1 wherein said retaining means includes a plurality of retaining elements each having a retainer opening dimensionally smaller than the diameter of the intravenous tubing so as to resistively impede the movement of the tubing into and out of the retaining element and having a retention cavity dimensionally larger than the diameter of the intravenous tubing so as to retain the tubing without deforming the tubing.

3. The device of claim 2 wherein said retaining elements include a plurality of paired notches opposingly formed in substantially parallel opposing spaced apart edges of a retention base member, said notches having a V-shaped retainer opening and a generally circular retention cavity.

4. The device of claim 2 wherein said retaining elements include a plurality of paired clips extending vertically from a retention base member, said clips opposingly aligned on said retention base member to form two spaced apart rows, said clips being generally U-shaped forming a generally circular retention cavity therein.

5. The device of claim 1 wherein said retaining means includes a selectively closable cover hingably attached to said removable retaining means, a surface of said cover when closed providing said surface for markable identification of the intravenous tubing retained in said retaining means.

6. The device of claim 1 wherein said retaining means includes a flap element having a living hinge, said hinge flexible to allow said flap to selectively cover said intravenous tubing as retained by said retaining means, a surface of said flap element when covering said intravenous tubing providing said markable surface for identification of the intravenous tubing retaining in said retaining means.

7. The device of claim 2 wherein said retaining elements include a plurality of retention channels formed in a retention base member, said channels forming a generally hexagonal retention cavity.

8. The device of claim 7 wherein said retention means includes a plurality of marking areas formed between said retention channels providing said markable surface for identifying the intravenous tubing retained adjacent to said marking area.

9. A device for organizing and identifying individual elements of a plurality of intravenous medication administration systems, comprising:
a bed portion, configured as a substantially planar area having a bottom planar element having a length and a width, an opposed pair of upwardly extending end wall elements spanning the width of said bottom planar element and disposed orthogonally to the plane of said bottom planar element, and an opposed pair of side elements spanning the length of said bottom planar element, said side elements and said end wall elements serving to bound said planar area so as to form an open topped rectangular parallelepiped;
a plurality of notches formed in a side element of said bed portion, said plurality being of a number equivalent to the multiplicity of flexible tubing lines that may be passed through said device, said plurality being distributed along the length of said side element in a substantially equidistantly spaced apart manner, each said notch being formed, in a direction of a thickness of said side element, to have a V-shaped opening, extending from an upper edge of said side element partially through the distance to said bottom planar element, and terminating in a substantially circularly arcuate opening through said side element, said V-shaped opening having a narrowest separation between bounding edges at its intersection with said arcuate opening; said circular arcuate opening being appropriately dimensioned to accept an outer diameter surface of a flexible tubing line therethrough without deforming constriction of said tubing, said narrowest separation between bounding edges of said V-shaped opening being marginally less than said tubing diameter;
a like plurality of identical notches formed in the other side element so as to be transversely, with respect to said bottom planar element, in registration with said plurality of notches formed in the first side element, each registering pair of notches in the opposed side elements forming a pathway through said device for a length of flexible tubing line;
a substantially planar rectangular cover portion element, having a rectangular area substantially equivalent to the area of said bottom planar element, said rectangular area having a corresponding length and width, said cover portion element further including an inner surface and an outer surface, both defined with respect to said bed portion;
means, formed on a first end wall element of said bed portion, for cooperating with said cover portion element to enable said cover portion element to be pivoted away from said bed portion to provide access to said notched pathways;
means, formed on a second end wall element of said bed portion, for cooperating with said cover portion element to enable said cover portion element to be releasably held proximate to said bed portion;
means, formed on a first longitudinal end of said cover portion element, for cooperatively engaging with said means formed on said first end wall element of said bed portion to enable said cover portion element to pivot upwardly from said bed portion about said first end wall element;
means, formed on a second longitudinal end of said cover portion element, for cooperatively releasably engaging with said means formed on said second end wall element of said bed portion to enable said cover portion to be releasably retained as a closing surface for said rectangular parallelepiped; and
a plurality, in like number as the number of flexible tubing pathways through said device, of substantially rectangular areas formed on said outer surface of said cover portion element, each rectangular area being surface textured to accept writings from common writing implements thereon, said texturing being further adapted to enable such writings to be readily removed by intentional obliteration thereof; each said rectangular area extending substantially across the width of said cover portion element; said rectangular areas being spaced apart along the length of said cover portion element so that each such rectangular area visibly overlays a corresponding pathway for a flexible tubing line through said device, said rectangular areas being separated by regions running across the width of said outer surface of said cover portion element that are not so surface textured, which regions are resistant to accepting writings thereon; and means for removably attaching said device to an appropriate supporting structure disposed proximate to the patient.

10. A device as claimed in claim 9, wherein said means for removably attaching said device to an appropriate supporting structure disposed proximate to the patient comprises a strap element coupled through said bed portion of said device in a manner not interfering with, or deforming, any flexible tubing lines passing through said device, said strap element being adapted to pass around any conveniently disposed vertically or horizontally oriented available supporting structure so as to secure said device positionally thereto.

11. A device as claimed in claim 10, further comprising means for coupling said bed portion of said device to said strap at a substantially mid-length position along the extent of said strap.

12. A device as claimed in claim 9, wherein said means for removably attaching said device to an appropriate supporting structure disposed proximate to the patient comprises a strap element disposed externally of said device and means for coupling an outer surface of said bottom planar element to said strap element at a substantially mid-length position along the extent of said strap, said strap element being adapted to pass around any conveniently disposed vertically or horizontally oriented available supporting structure so as to secure said device positionally thereto.

13. A device as claimed in claim 9, wherein said means for removably attaching said device to an appropriate supporting structure disposed proximate to the patient comprises:

a first mating and engaging element substantially rigidly coupled to an outer surface of said bottom planar element of said bed portion of said device; and a second mating and engaging element relocatably affixable to a convenient surface area of said supporting structure;

said first mating and engaging element and said second mating and engaging element being mutually adapted to mate and engage with each other so as to retain said device positionally with respect to said supporting structure; said mating and engaging of said first and second elements being manually releasable.

14. A device as claimed in claim 13, wherein said first mating and engaging element is an area distribution of loops of a hook and loop type fastening system, disposed substantially uniformly across the area of said outer surface of said bottom planar element, and wherein said second mating and engaging element is a like area distribution of hooks of a hook and loop type fastening system removably affixable on a surface area of said supporting structure.

15. A device as claimed in claim 14, wherein said hooks are replaced by said loops and said loops are replaced by said hooks.

16. A device as claimed in claim 9, wherein said means for removably attaching said device to an appropriate supporting structure disposed proximate to the patient comprises a distributed adhesive applied substantially uniformly across an outer surface of said bottom planar element of said bed portion of said device, said adhesive being adapted to adhere to typical surfaces found on common surfaces of generally available supporting structures in a sickroom; said adhesive being further adapted to enable manual removal of said device from said supporting structure.

17. A device as claimed in claim 9 formed as a single integral structure that may be coupled to said means for removably attaching said device to an appropriate supporting structure disposed proximate to the patient.

* * * * *

UNITED STATES PATENT AND TRADEMARK OFFICE
CERTIFICATE OF CORRECTION

PATENT NO.   : 5,224,674
DATED        : July 6, 1993
INVENTOR(S)  : RAMONA K. SIMONS It is certified that error appears in the above-indentified patent and that said Letters Patent is hereby corrected as shown below:

Column 1, line 26, "facilitates" should be --facilities--.

Column 5, line 8, after "portion" delete "," and insert --.--.

Column 5, line 27, delete "is".

Signed and Sealed this

Twenty-second Day of March, 1994

Attest:

BRUCE LEHMAN

Attesting Officer     Commissioner of Patents and Trademarks